US009255898B2

(12) United States Patent
Coquerel et al.

(10) Patent No.: US 9,255,898 B2
(45) Date of Patent: Feb. 9, 2016

(54) METHOD OF MEASURING SCATTERING OF X-RAYS, ITS APPLICATIONS AND IMPLEMENTATION DEVICE

(75) Inventors: Gerard Coquerel, Boos (FR); Morgane Sanselme, Bois Guillaume (FR); Anais Lafontaine, Rouen (FR)

(73) Assignee: UNIVERSITE DE ROUEN, Mont-saint-aignan (FR)

( * ) Notice: Subject to any disclaimer, the term of this patent is extended or adjusted under 35 U.S.C. 154(b) by 183 days.

(21) Appl. No.: 14/009,383

(22) PCT Filed: Apr. 2, 2012

(86) PCT No.: PCT/FR2012/050707
§ 371 (c)(1),
(2), (4) Date: Oct. 2, 2013

(87) PCT Pub. No.: WO2012/136921
PCT Pub. Date: Oct. 11, 2012

(65) Prior Publication Data
US 2014/0185768 A1    Jul. 3, 2014

(30) Foreign Application Priority Data
Apr. 6, 2011  (FR) .................................. 11 53007

(51) Int. Cl.
*G01N 23/20*  (2006.01)
*G01N 23/203*  (2006.01)
*G01N 23/207*  (2006.01)

(52) U.S. Cl.
CPC ............. *G01N 23/203* (2013.01); *G01N 23/20* (2013.01); *G01N 23/207* (2013.01); *G01N 23/20033* (2013.01); *G01N 2223/056* (2013.01); *G01N2223/1016* (2013.01); *G01N 2223/602* (2013.01); *G01N 2223/639* (2013.01)

(58) Field of Classification Search
CPC ............ G01N 23/20; G01N 23/20008; G01N 23/20016; G01N 23/20025; G01N 23/20033; G01N 23/203; G01N 23/207; G21K 1/06
USPC ........... 378/70, 71, 73, 76, 79, 80, 81, 83, 86, 378/88
See application file for complete search history.

(56) References Cited

U.S. PATENT DOCUMENTS

| 3,112,398 | A | 11/1963 | Shimula |
| 7,113,265 | B1 | 9/2006 | Sarrazin et al. |
| 7,838,843 | B2 | 11/2010 | Kawakami et al. |

FOREIGN PATENT DOCUMENTS

| JP | 10-38772 | 2/1998 |
| JP | 3-685422 | 8/2005 |

OTHER PUBLICATIONS

English Machine Translation of Japanese Patent JP 10-038772.
English Machine Translation of Japanese Patent JP 3-685422.

*Primary Examiner* — Jurie Yun
(74) *Attorney, Agent, or Firm* — Frost Brown Todd LLC

(57) ABSTRACT

The present invention relates to a method and a device for measuring scattering of X-rays wherein the compound to be analyzed is installed in a receptacle comprising an X-ray-permeable flat bottom, wherein the X-ray diffraction analysis is undertaken by sending an X-ray stream upwards toward said X-ray-permeable bottom and by measuring the stream of scattered X-rays reflected downwards, and wherein a fluid thermostatically controlled to the same temperature as that of the compound to be analyzed in the receptacle is projected toward the X-ray permeable flat bottom, from outside the receptacle.

16 Claims, 9 Drawing Sheets

METHOD OF MEASURING SCATTERING OF X-RAYS, ITS APPLICATIONS AND IMPLEMENTATION DEVICE

The present invention relates to a method of measuring scattering of X-rays, its applications and an implementation device.

The solid form of chemical compounds is by far the most used form. Customarily, chemical compounds are manufactured after a series of reactions in a liquid medium, at the end of which the chemical compounds are obtained in solid, crystalline or amorphous form.

It is of great interest, in particular in the pharmaceutical industry, to track the crystallization of compounds. To best manage the crystallization of a chemical compound, it is necessary to track what happens when the product is in suspension.

Several technologies dedicated to the in situ tracking of crystallization have been developed over recent years, for example RAMAN or NIR. But none of these techniques is as precise and exact as X-ray diffraction. However, to date, there does not exist any in situ device making it possible to track the crystallization of a chemical compound by X-ray diffraction with a laboratory X-ray source. The devices already in existence require either the use of synchrotron radiation, or a recirculation loop external to the reactor where the reaction occurs, such as the PreFIX Slurry Flow Cell® technique from the company Panalytical. One of the difficulties with the in situ tracking of a crystallization stems from the fact that the crystallization occurs in a liquid medium.

The article In-situ Monitoring of the formation of Crystalline Solids N. Pienack, W. Bensch, Angew. Chem. Int., 2011, 50, 2-23 describes the main ways of tracking a crystallization in situ.

Recall that X-ray diffractometry is an analysis technique based on the diffraction of X-rays on crystalline matter involving a measurement apparatus called a diffractometer. Conventionally, a diffractometer essentially comprises a part serving to perform the measurement (goniometer, XR source, sample holder, detector) and an electrical part (generator, cooling circuit, computer boards).

JP 3 685422 B2 and JP 10 038772 describe diffractometers allowing XR analysis from underneath, but the diffractometer of JP 10 038772 is not compatible with a reactor where a crystallization process could be carried out, since the sample holder performs a rotation during the analysis. The diffractometer of JP 3 685422 does not make it possible to track the evolution of the solid phases in suspension or in equilibrium with a gas as a function of temperature, of solvent, of stirring, of humidity.

After lengthy research the applicant has fine-tuned a technique based on X-ray diffraction allowing excellent discrimination between the solid phases (crystallized, amorphous, semi-crystalline, etc.) present during the various steps of a precipitation-crystallization process, and has fine-tuned a device to this end. The technique of the invention is utilizable even with a solid sample of low mass (for example about 1 mg), in particular when the sample is in equilibrium with a gas of fixed composition and is consequently sensitive to the regulating conditions in terms of composition of the gas (for example humidity) and in terms of temperature.

This is why the subject of the present patent application is a method of measuring scattering of X-rays, characterized in that a compound to be analyzed is installed in a receptacle comprising an X-ray-permeable flat bottom, and an X-ray diffraction analysis is undertaken by sending an X-ray stream upwards toward said X-ray-permeable bottom and by measuring the stream of scattered X-rays reflected downwards.

Recall that in X-ray diffraction analyses, the angles of incidence and of reflection, which moreover are equal, are made to vary.

More precisely, a fluid thermostatically controlled to the same temperature as that of the compound to be analyzed in the receptacle is projected toward the X-ray-permeable flat bottom, from outside the receptacle.

The compound to be analyzed can at the start of the method be present in solution, in suspension in one of its solvents, as an emulsion or in the pulverulent state under a controlled atmosphere.

Under preferential conditions of implementation of the invention, the X-ray-permeable flat bottom is installed horizontally.

To undertake the measurement, the displacement of the source and of the symmetric detector with respect to the vertical is performed for example according to angles (Bragg angles) with respect to the horizontal of from −0.5 degrees to −70 degrees, in particular from −3 degrees to −50 degrees in terms of a 2 Theta angular scale. Recall that in X-ray diffraction, angles are referred to the horizontal.

According to the measurement performed, the X-ray generator sends X-rays onto the compound to be analyzed for a duration of for example a few minutes to several hours.

The wavelength of the X-rays used is for example 1.5405 angströms (copper anticathode), 0.5594 angströms (silver anticathode), 0.7093 angströms (molybdenum anticathode). The beam can be monochromatic $K\alpha1$ or a preferably close wavelength mixture, for example $K\alpha1$ and $K\alpha2$.

Under preferential conditions of implementation of the method, the receptacle used is provided with a thermoregulating device which makes it possible to fix at a constant the temperature—isothermal mode—and also to apply a temperature gradient to track a polythermic method. To this end, the receptacle used is for example provided with a double jacket allowing the circulation of a heat-transfer fluid.

A fluid, preferably a gas, such as air or nitrogen for example, is projected toward the X-ray-permeable flat bottom, from outside the receptacle. Thus, under certain humidity conditions, the condensation on the flat bottom is limited. The gas can advantageously be dry. The fluid, preferably gas, is thermostatically controlled to afford better thermal regulation of the system. The fluid is preferably thermostatically controlled to the same temperature as that of the compound to be analyzed in the receptacle. Thus, the technique of the invention is utilizable even with a solid sample of low mass (for example about 1 mg), in particular when the sample is in equilibrium with a gas of fixed composition and is consequently sensitive to the regulating conditions in terms of composition of the gas (for example humidity) and in terms of temperature.

In the method which is the subject of the present invention, the sample holder is not mobile during the analyses, thereby making it possible to study a crystallization process.

The compound to be analyzed can generally be a solid substance or a mixture of solid substances, more particularly a crystallized compound or a mixture of several crystallized compounds.

The method which is the subject of the present invention possesses very beneficial qualities and functionalities. The in situ tracking of the formation or evolution of the solids in their medium makes it possible to limit the effects inherent in the sampling of the solid during a study. Because the X-rays originate from underneath and because the diffraction is also measured from underneath, it is possible to analyze the solids in their real states, for example efflorescent solids which are not stable outside of their mother solution. The possibility of thermostatic control makes it possible furthermore to carry out the majority of crystallization processes in continuity with their manufacture.

The ports present on the cover of the crystallization tracking device make it possible to carry out additions of liquid or solid and also make it possible to couple the analysis with other measurement probes (pH, temperature, NIR, FBRM etc.).

Thus the method which is the subject of the present invention makes it possible to characterize the solid phases and to track their evolutions with a conventional scattering source. This takes into account polymorphic transformations, the formation of co-crystals, binary, ternary and higher-order peritectic transitions, eutectoid transitions, peritectoid transitions, formations of inclusion compounds, solvations or hydrations, desolvations or dehydrations, exchanges of solvents within the crystallized phases or else the evolution of the amorphous forms into crystalline phases.

It furthermore makes it possible to verify the stability of the crystallized compounds as a function of the matrix in which it is situated (liquid, gas, gel, emulsion, amorphous solid).

It likewise makes it possible to detect the metastable phases and the reaction intermediate phases.

It also makes it possible to track the formation or the evolution of salts during variations of pH.

It makes it possible to easily track the formation of all the transient, metastable or stable crystallized species to which the precipitation methods are liable to give rise.

The sample holder not being mobile for the duration of the analyses, it is possible to study a crystallization process.

The thermo-regulated fluid stream sent onto the lower external face of the membrane ensures effective and precise thermal regulation of a solid in contact with the X-ray-permeable bottom. Indeed, the stream makes it possible to control dynamically or statically, or dynamically and statically the temperature of the bottom against which it is sent.

These qualities and functionalities are illustrated hereinafter in the experimental part.

They justify the use of the methods described hereinabove, in particular in the tracking of crystallization processes, in the tracking of polymorphic evolutions or of solvation, in the study of stability of a system in a matrix which is defined, if desired as a function of temperature, in the search for metastable phases or reaction intermediaries, in the study of the evolution of salts as a function of pH.

In the present patent application, "mother liquor" is understood to mean saturated solution which is in equilibrium with the solid in suspension.

In particular in the field of pharmaceutical production, the method of the present invention makes it possible to know whether only the desired phase or phases and not others are present when tracking the manufacture of crystallized compounds. It is then possible to establish a list of peaks on the diffractogram of an unknown product, that can be compared with a list of peaks established on the diffractogram of a reference product.

This is why the subject of the present patent application is also the use of the method described hereinabove for the tracking of a crystallization process.

The subject of the present patent application is also the use of the method described hereinabove for the tracking of polymorphic evolutions or solvation.

The subject of the present patent application is furthermore the use of the method described hereinabove for the study of stability of a solid phase in a matrix such as liquid, gas, gel, emulsion or amorphous solid.

The subject of the present patent application is also the use of the method described hereinabove for the search for metastable phases or reaction intermediaries.

The subject of the present patent application is also the use of the method described hereinabove for the study of the evolution of salts as a function of pH.

The subject of the present patent application is also the use of the method described hereinabove for the study of the evolution of the crystals of a protein as a function of ionic strength or of pH or of an anti-solvent or of several of these parameters, in particular two parameters.

The subject of the present patent application is also the use of the method described hereinabove for the study of the evolution of salts as a function of the composition in terms of solvent and/or constituents of all sorts liable to give rise to the formation of at least one solid.

The subject of the present patent application is also a device designed for the implementation of the method described hereinabove characterized in that it comprises a receptacle comprising a bottom plugged by an X-ray-transparent membrane, as well as a diffractometer provided with a goniometer installed so as to direct a beam of X-rays from underneath toward the X-ray-transparent membrane and the detector being installed so as to measure the X-rays scattered from underneath.

According to the present invention, elements of a conventional diffractometer that are used for measurement have been modified. The way in which the goniometer is oriented has been modified with respect to a goniometer found in standard powder-based diffraction systems. Consequently, the particular receptacle hereinabove has been designed, in which it is possible to carry out crystallizations that it is possible to track according to the method which is the subject of the present patent application.

Thus, the goniometer of the X-ray diffractometer exhibits a -theta/-theta or else inverted reflection based geometry for directing a beam of X-rays toward the X-ray-transparent membrane.

Said receptacle comprises means for heating or cooling the content. With this aim, advantageously said receptacle comprises a double wall allowing the circulation of a heat-transfer fluid. In such a case, a heat-transfer fluid inlet port and outlet port are advantageously envisaged. A temperature regulating system of thermostat-cryostat type can be linked to the receptacle. This system is advantageously programmable so as to make it possible to carry out a temperature program, this comprises in particular the possibility of performing an increasing or decreasing gradient, a temperature cycle, an isotherm, etc.

Under preferential conditions of implementation of the invention, the bottom of the receptacle hereinabove comprises a circular opening plugged by the X-ray-transparent membrane. This opening can have a diameter of 0.5 to 5 cm, preferably of the size of the incident beam.

The X-ray-transparent membrane is fixed in such a way that it is as flat as technically possible.

Under other preferential conditions of implementation of the invention, the device hereinabove furthermore comprises a stirrer. Under other preferential conditions of implementation of the invention, the device hereinabove furthermore comprises means for closing the receptacle. These means for closing the receptacle make it possible to render the latter in particular leaktight to liquids and optionally to gases.

The device hereinabove comprises a port for the installation in particular of a temperature probe (termed the internal temperature probe). An external temperature probe is advantageously placed near the X-ray-transparent window so as to ensure precise temperature regulation of the external fluid projected thereonto. Under yet other preferential conditions of implementation of the invention, the device hereinabove comprises several ports for the installation in particular of one or more probes. The device preferably comprises two or three ports.

The device hereinabove comprises outside the receptacle one or more nozzles for projecting a fluid, preferably a gas, such as air or nitrogen for example, toward the X-ray-permeable flat bottom, from outside the receptacle. Under still other preferential conditions of implementation of the invention, the device hereinabove comprises several nozzles.

The receptacle then comprises an internal temperature probe serving to match the temperature of the compound to be analyzed and that of the external fluid. The probe can then communicate the temperature of the compound to a projected-fluid temperature regulating device. An external temperature probe can be placed near the X-ray-transparent window to ensure the control of the temperature of the external fluid thermo-regulated by virtue of a second regulating system. The external temperature probe must obviously not impede the X-ray beam.

According to the height of the content in the receptacle, the X-ray-transparent membrane subjected to a pressure may sag. Preferably, the X-ray-transparent membrane is fixed to the receptacle in such a way that the former is perfectly flat and horizontal.

The X-ray-transparent membrane exhibits properties suited to the use of the device. It preferably exhibits properties of chemical and physical resistance, in particular: resistance to solvents and chemical products placed in the receptacle, if necessary resistance to temperature, undeformability, weak elasticity, resistance to tensions, resistance to the abrasion effect of powder in motion and to tearing. It advantageously exhibits more than four, in particular more than five, more particularly all of these properties. Materials which exhibit the main quality, transparency to X-rays and other qualities cited above are for example, a polyimide (Kapton®; Chemplex), or a polyethylene terephthalate (Mylar®; Chemplex).

The probe is for example chosen from among pH probes, FBRM® (Focused Beam Reflectance Measurement) probes, viscosity probes, near infrared (NIR) probes, humidity or internal temperature probes, in particular the latter so as to communicate the temperature of the compound to a device for regulating the temperature of the external fluid projected onto the window.

Under yet other preferential conditions of implementation of the invention, the device hereinabove comprises one or more probes chosen from among the probes cited above.

Under yet other preferential conditions of implementation of the invention, the device comprises a platform mobile in the three directions x, y and z in space so as to be able to adjust the location, mainly in terms of z, of the X-ray-transparent bottom.

Note that in the present patent application, conventionally the indefinite article "a" must be considered to be a generic plural (meaning "at least one" or else "one or more"), except when the context shows the contrary (1 or "a single"). Thus, for example, when it is stated hereinabove that there is provision for a probe, this signifies one or more probes.

The preferential conditions of implementation of the methods described hereinabove also apply to the other above-envisaged subjects of the invention, in particular to the devices designed for the implementation of these methods and vice versa, as well as to their applications.

The invention will be better understood on referring to the appended drawings in which FIG. 1 represents a diagram of an implementation device of the invention according to two orientations, FIG. 2 represents a diagram of a receptacle usable in the implementation device of the invention, FIG. 3 represents an overall diagram of an implementation device of the invention.

Figure 10:
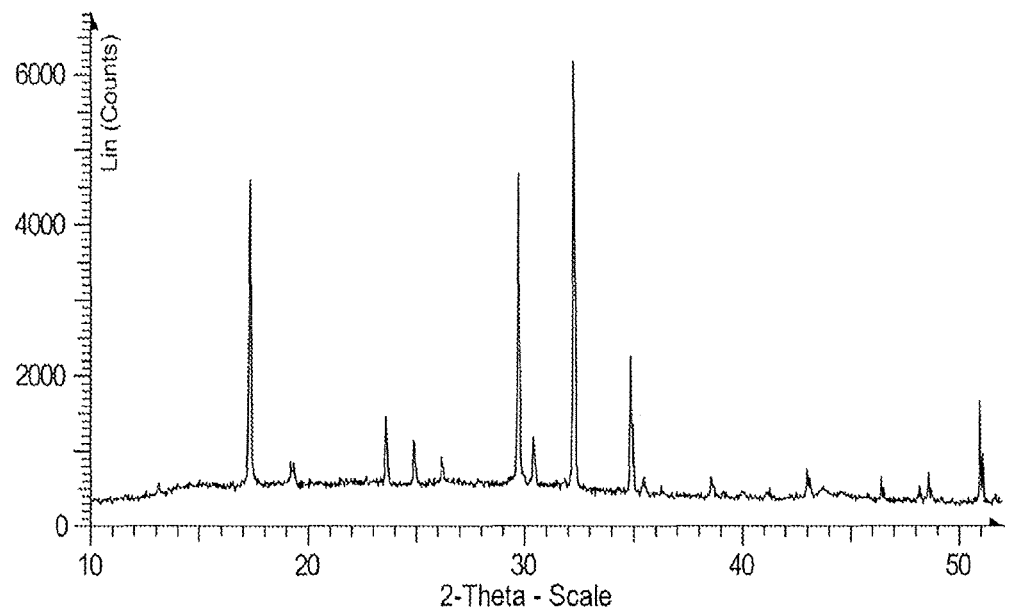
Figure 11:
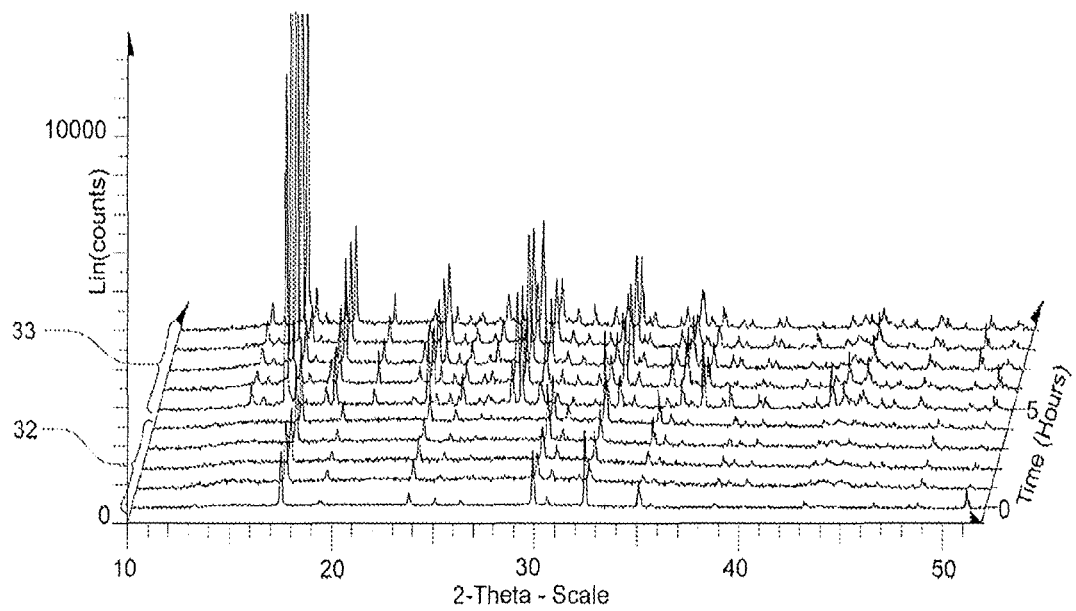
Figure 12:
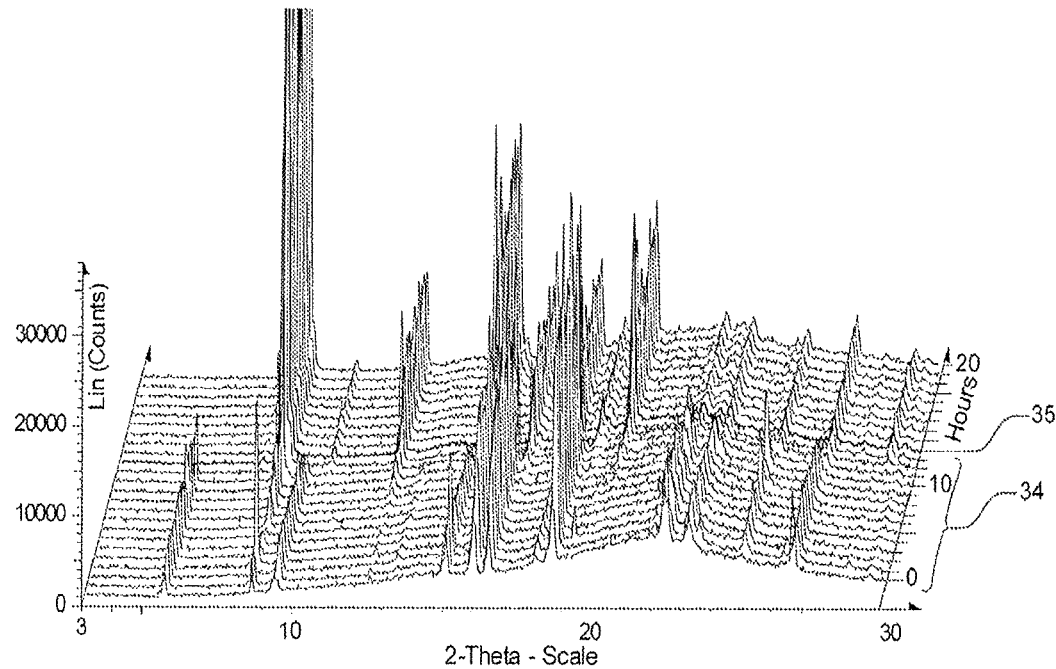
Figure 13:
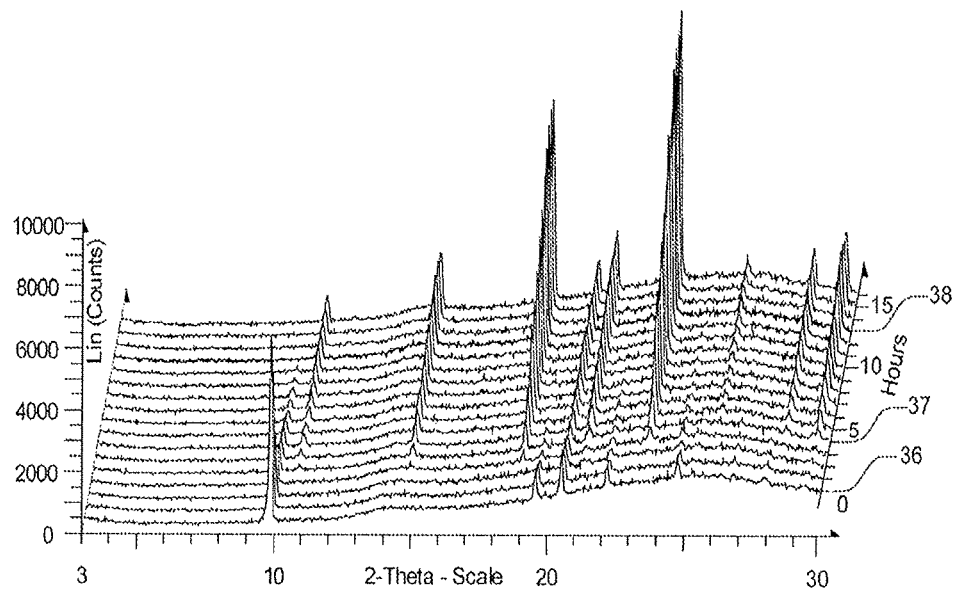

FIG. 10 represents the first diffractogram obtained after detection of the exothermic phenomenon of Example 3, FIG. 11 represents the diffractograms recorded during the isotherm at 18° C. of Example 3 as a function of time, FIG. 12 represents the diffractograms obtained as a function of time during the evolution of a mixture of two polymorphs of pleconaril 34 to a single of these polymorphs 35 in ethanolic solution, FIG. 13 represents the diffractograms obtained as a function of time during the monotropic transition of D-mannitol in suspension in a water/methanol mixture.

Figure 14:
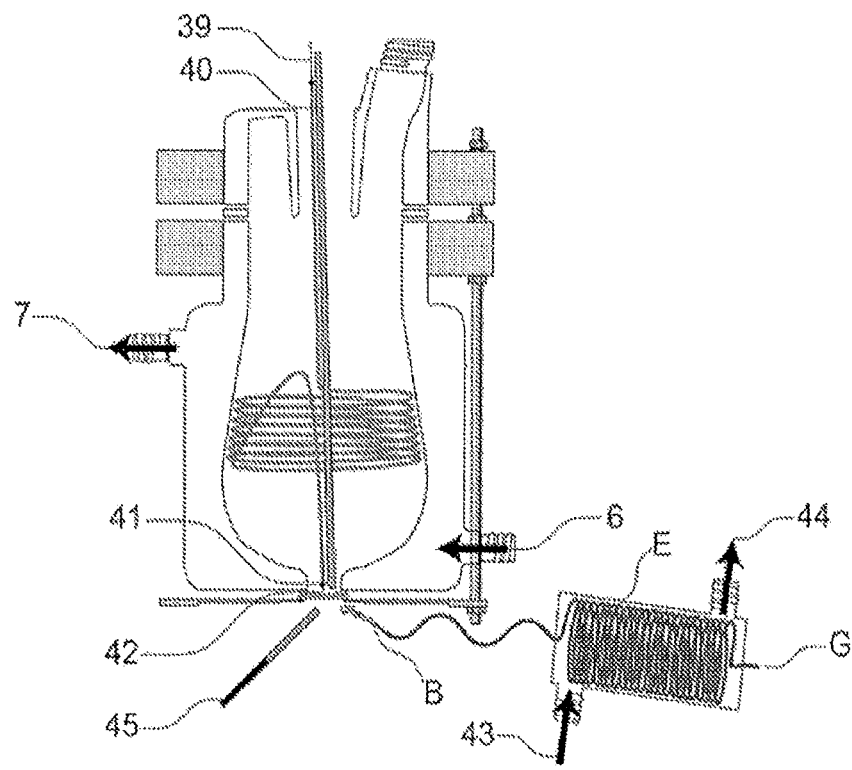

FIG. 14 shows diagrammatically a receptacle usable in the implementation device of the invention more specifically useful for the analyses of solids in equilibrium with a gas regulated in terms of composition and temperature.

Figure 15:
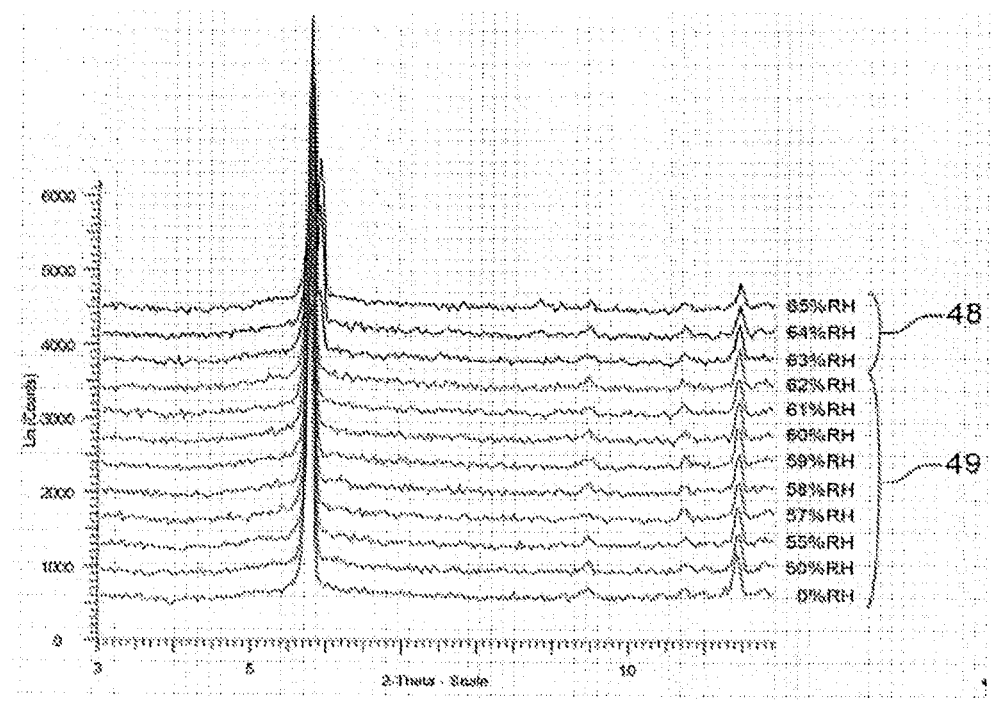
Figure 16:
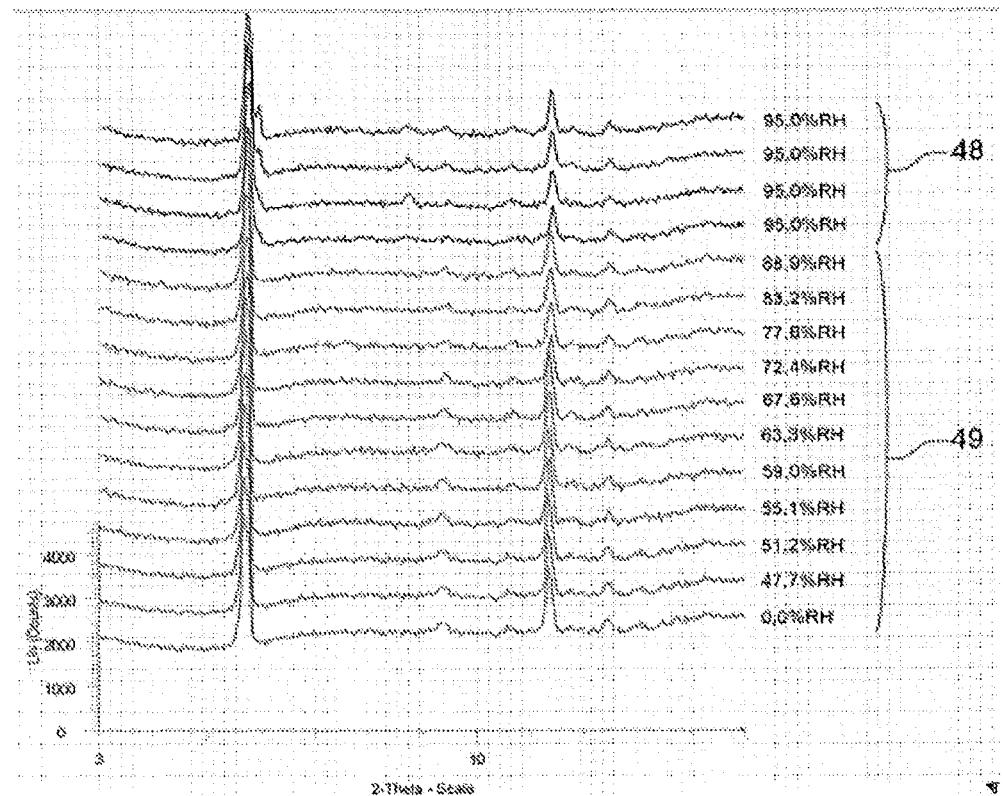
Figure 17:
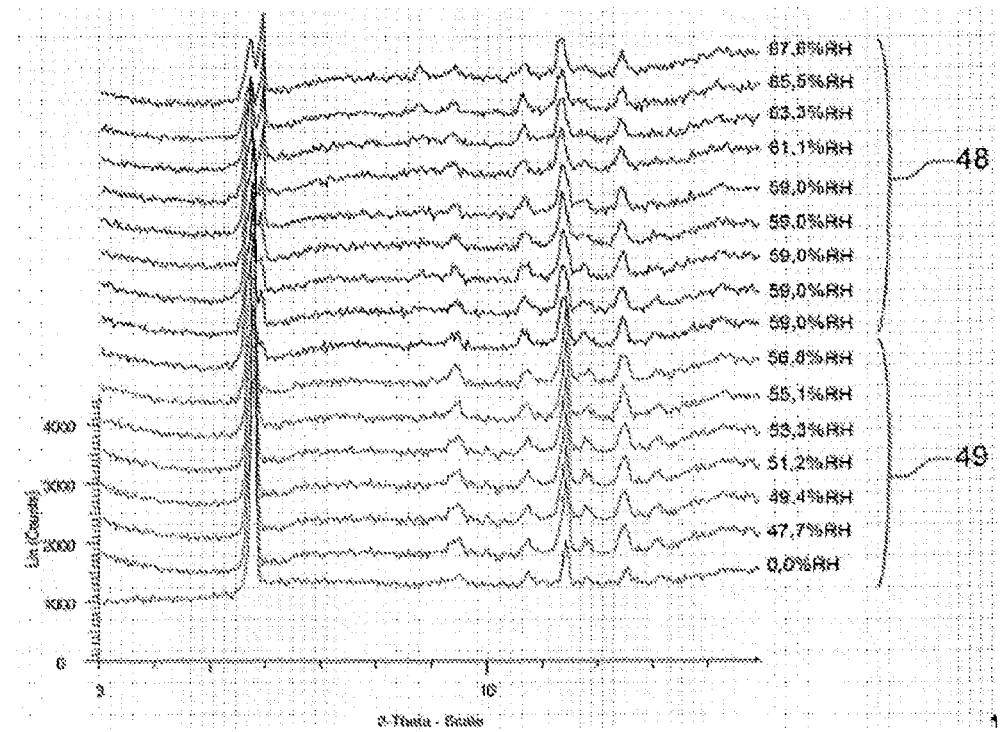

FIG. 15 represents the diffractograms of BrHPP Benz obtained in Example 6 in the course of the hydration of BrHPP Benz with the temperatures of internal humid gas and of external dry gas regulated to 25° C., FIG. 16 represents the diffractograms of BrHPP Benz obtained in Example 6 in the course of the hydration of BrHPP Benz at 5° C. with the temperature of external dry gas not thermo-regulated, FIG. 17 represents the diffractograms of BrHPP Benz obtained in Example 6 in the course of the hydration of BrHPP Benz at 5° C. with the temperature of external dry gas thermo-regulated.

Figure 1:
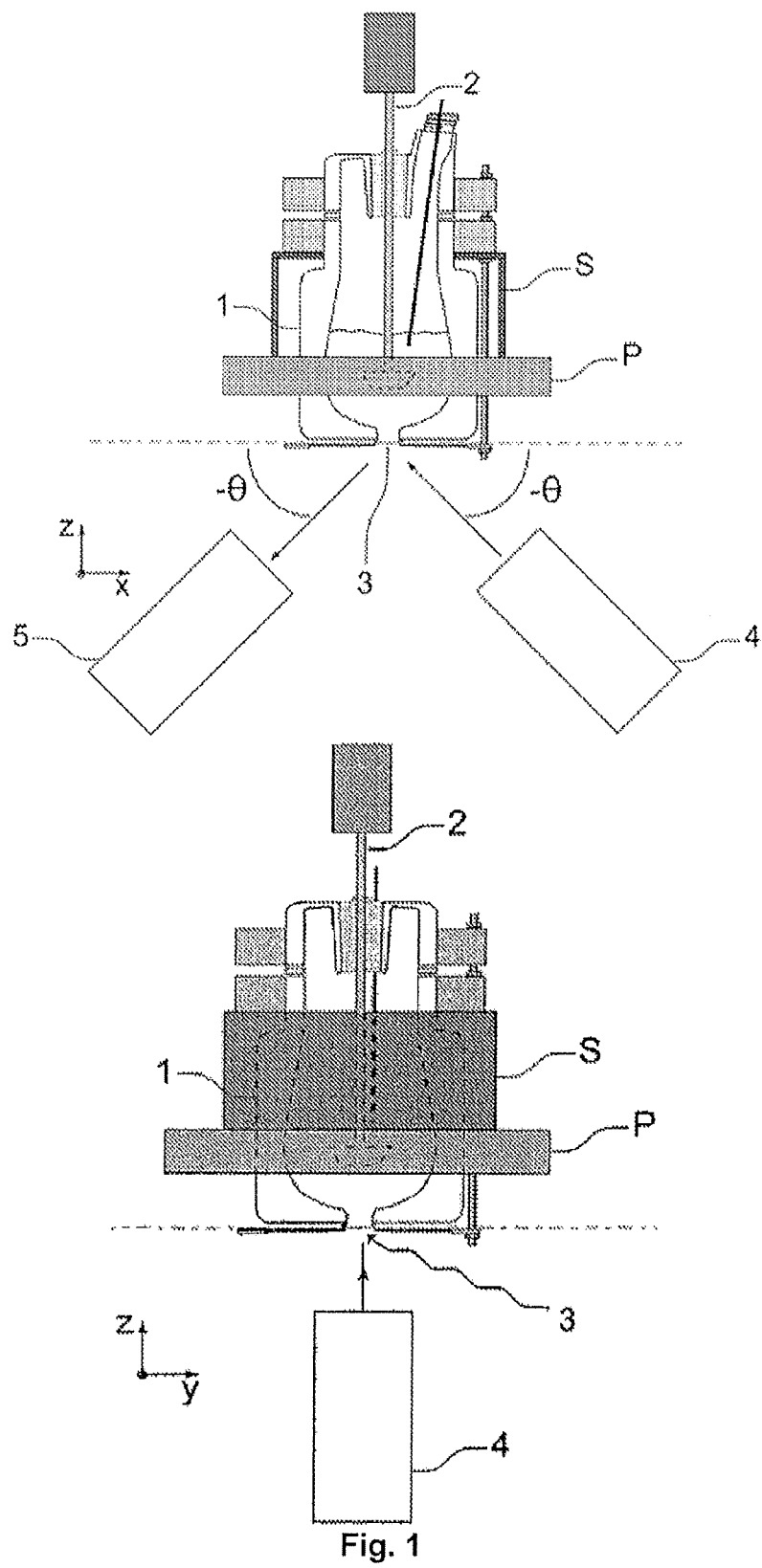

FIG. 1 depicts a double-walled receptacle 1 provided with a stirrer 2 and its motor. The bottom of the receptacle 1 is plugged by an X-ray-transparent membrane 3, made here from Kapton®. The receptacle 1 rests on the xyz stage P by way of a metallic support S.

An X-ray source 4 is placed under the membrane 3, as is an X-ray detector 5. The X-ray source 4 used here is marketed by the company Siemens under the brand name KFLCu2K399-689®, installed in a sheath marketed by the company Bruker under the brand name C79298-A3244-A4®, and the X-ray detector 5 used here is a fast detector marketed by the company Bruker under the brand name LynxEye®.

With respect to the horizontal indicated by dots, the angles of incidence of the X-rays are negative and equal, thereby justifying the term "-theta/-theta" where theta is the angle of incidence.

Figure 2:
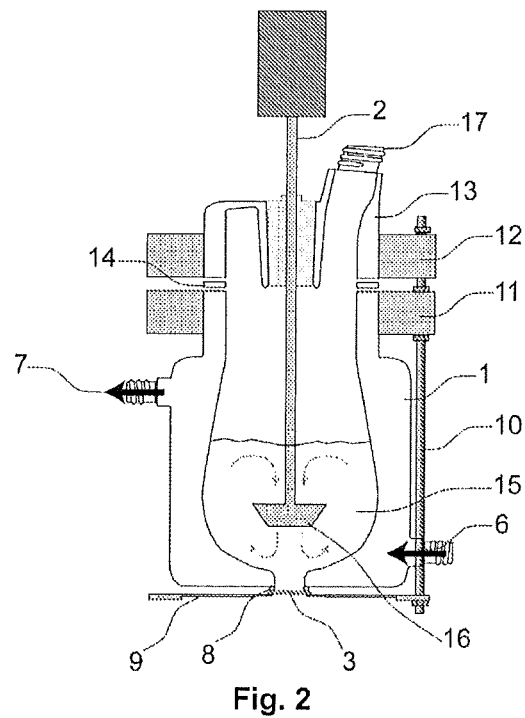

FIG. 2 depicts more clearly the double-walled receptacle 1 provided with a stirrer 2 and its motor represented above. It is provided with an inlet 6 and with an outlet 7 able to serve for the circulation of a heating or cooling fluid. The bottom of the receptacle 1 is plugged by the X-ray-transparent membrane 3. The leaktightness of the bottom is ensured by an O-ring seal gripped between the bottom of the receptacle 1 and a plate 9. The gripping is carried out here using a system associating threaded rods 10 which cooperate with a system of clamps. The lower clamp 11 also holds the upper neck of the double-walled receptacle 1. The upper clamp 12 holds the cover 13 and makes it possible to press a PTFE seal 14 to ensure leaktightness in the upper part of the receptacle 1. The threaded rods 10 and the lower clamp 13 also make it possible to fix the receptacle 1 to the metallic support S. The solution, suspension, or other system with n constituents, which is being studied 15, is installed in the receptacle 1 and kept if desired continuously stirred by the blades 16 of the stirrer 2.

The upper opening 17 allows for example the insertion of probes, the addition or the removal of products, for example the addition of solvent.

Figure 3:
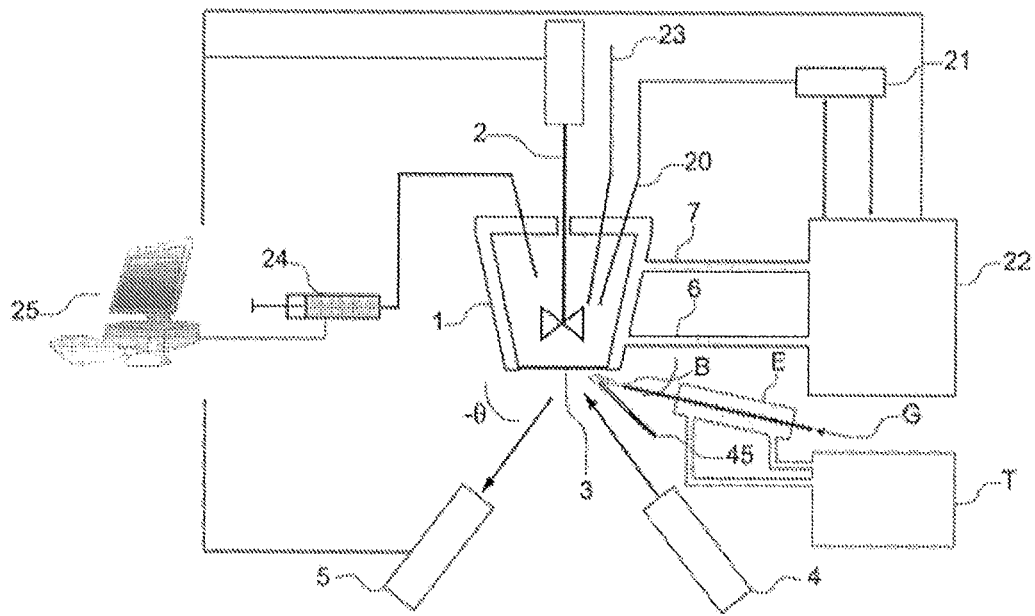

FIG. 3 shows diagrammatically a more complete arrangement. In addition to the elements of FIG. 1 there is an internal temperature probe 20 connected to a control device 21 itself linked to a temperature regulating system 22 allowing the circulation of a heat-transfer fluid through the inlet 6 and the outlet 7. A second thermo-regulating system T makes it possible to regulate the temperature of a current of fluid G projected onto the external wall of the window 3 by virtue of a heat exchanger E. The temperature of this fluid is controlled at the level of the window 3 by an external temperature probe 45 so that the temperature is identical to that of the compound to be analyzed in the receptacle 1. This thermostatically controlled fluid is projected toward the X-ray-permeable flat bottom 3, from outside the receptacle 1, with the aid of a nozzle B placed in proximity to the receptacle. Another probe 23 has been installed. An ancillary device consisting here of a pump 24 allows the injection for example of solvent. A computer 25 captures, records, analyzes and transmits data. It is linked in particular to the detector 5 and to the X-ray source 4, to the temperature probe 20, to the thermostat system 22. It can also be linked in particular to the motor of the stirrer as well as to the pump 24.

In FIG. 14 is represented an adaptation of the double-walled receptacle of FIG. 1 more specific for gas/solid systems. A humid fluid stream 39 is sent into a receptacle and is thermostatically controlled to attain the temperature and the humidity desired on its arrival 41 in contact with a sample 42. A humidity probe and an internal temperature probe 39 make it possible to ensure the control of relative humidity and of the temperature inside the chamber in contact with the solid to be analyzed 42. To ensure proper control of the temperature of the sample 42 and avoid possible condensation on the external face of the XR permeable membrane, a thermostatically controlled gaseous fluid stream G via a heat exchanger E is sent onto the external wall of the window through a nozzle B. The temperature of this gaseous fluid is regulated via a measurement by an external temperature probe 45.

The examples of implementation which follow illustrate the present patent application.

After any arrangement of the transparent film on the receptacle, the height of the X-ray-transparent bottom of the receptacle is adjusted before carrying out the experiments. Accordingly, an ethanolic suspension of sodium chloride can for example be used. X-ray diffraction analyses are carried out between 25° and 35° in terms of 2Theta at various heights z to obtain the proper value of the peak (002) of the sodium chloride at 31.791° in terms of 2Theta. The receptacle is thereafter washed without removing the film.

EXAMPLE 1

Tracking of a Sodium Sulfate Suspension with a View to Characterizing an Efflorescent Solvate In a receptacle of FIG. 2 arranged as shown diagrammatically in FIG. 3, 43.1 g of anhydrous sodium sulfate were added to 70 mL of water heated to 35° C. while stirring at 1000 rpm and the receptacle reclosed in a leaktight manner. After 10 minutes of stirring, the suspension obtained was cooled from 35° C. to 26° C. in 12 minutes. Next it was maintained in isotherm at 26° C. The temperature was regulated by way of a cryostat F32-HE® marketed by the company Julabo. Here, regulation was carried out on the internal temperature of the cryostat. To carry out the stirring, an axial turbo-stirring rod R 1311® marketed by the company IKA is used with a mechanical motor RZR2051 Control® marketed by the company Heidolph.

Once the temperature had stabilized, to observe the evolution of the sodium sulfate, an X-ray diffraction analysis was performed while continuing to stir the medium at 1000 rpm. The X-ray source used here is marketed by the company Siemens under the brand name KFLCu2K399-689® positioned in a sheath marketed by the company Bruker under the brand name C79298-A3244-A4®, and the X-ray detector used here is a fast detector marketed by the company Bruker under the brand name LynxEye®. The diffractometer as a whole is controlled by the XRDCommander® software marketed by the company Bruker. This type of device and software is commonly used within the framework of conventional X-ray diffractometries. The analyses are carried out between $-10°$ and $-52°$ in terms of a 2 Theta angular scale, with intervals of $0.038°$, the acquisition times being 0.5 s per interval. During the measurement, the incident X-ray stream and the detector remained symmetric with respect to the vertical passing through the flat bottom of the receptacle and oriented upwards toward said X-ray-permeable flat bottom, itself positioned horizontally.

The temperature regulated in the thermostat and the temperature of the suspension inside the reactor have been recorded in parallel.

Figure 4:
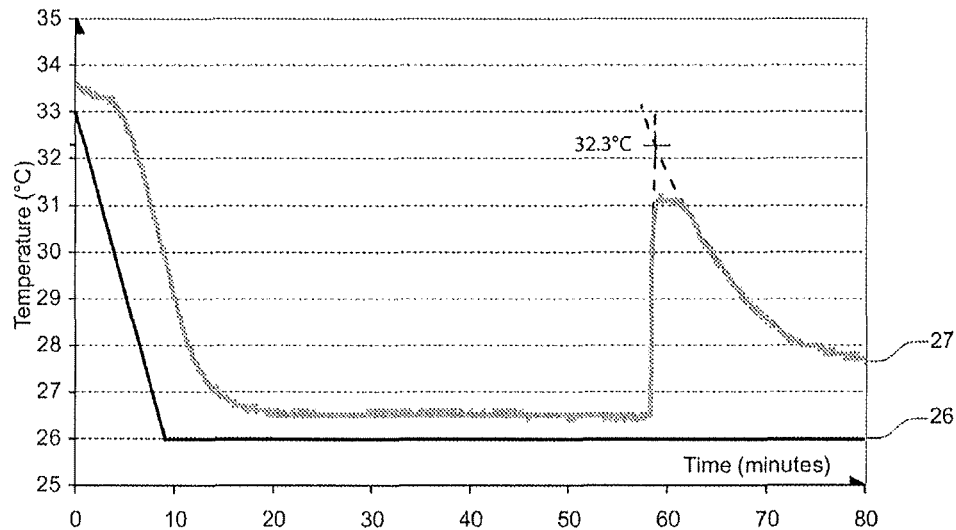
FIG. 4 represents the tracking curves of the internal temperature of the thermostat 26 and in the reactor 27 during the evolution of anhydrous sodium sulfate into sodium sulfate decahydrate.

The temperature curves are represented in FIG. 4. Tracking of the temperature regulated in the thermostat 26 and of the temperature obtained inside the reactor 27 shows that an exothermic phenomenon occurred in the reactor after 40 minutes at 26.5° C. The diffractograms represented in FIG. 5 obtained on the suspension and after this phenomenon show that the latter corresponds to the transition of anhydrous sodium sulfate to sodium sulfate decahydrate.

It is deduced therefrom that the present in situ device for X-ray diffraction analysis makes it possible to track the evolution of an anhydrous phase into a hydrated phase.

Figure 5:
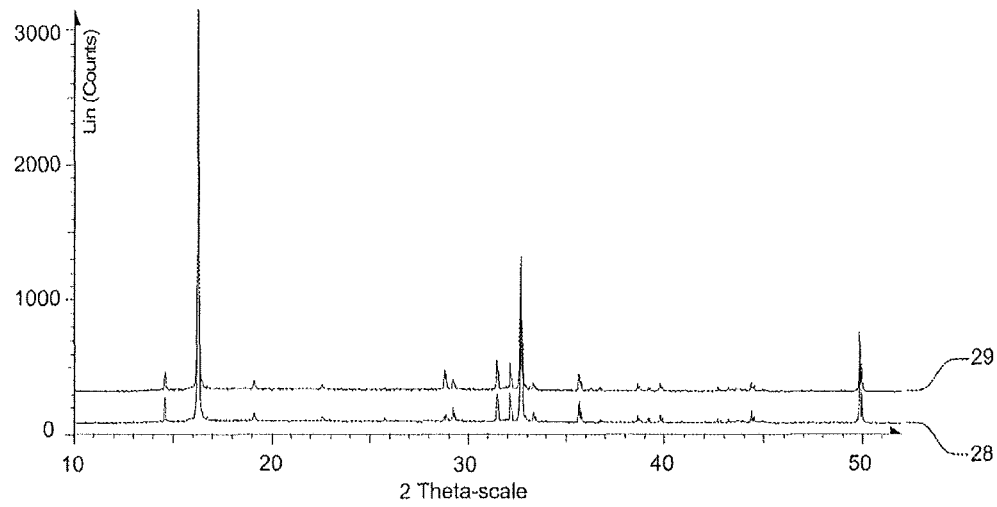
FIG. 5 represents the diffractograms obtained without stirring 28 and with stirring 29 of the sodium sulfate decahydrate in aqueous suspension.

The formation of the hydrate leading to the formation of big crystals, the suspension had a tendency to clump when stirring was halted. However, the diffractograms of FIG. 5 show the results obtained without stirring 28 and with stirring 29 are identical.

It is deduced therefrom that stirring has no influence on the quality and the correctness of the results obtained. Consequently the in situ analyses by X-ray diffraction can be carried out either with or without stirring.

Figure 6:
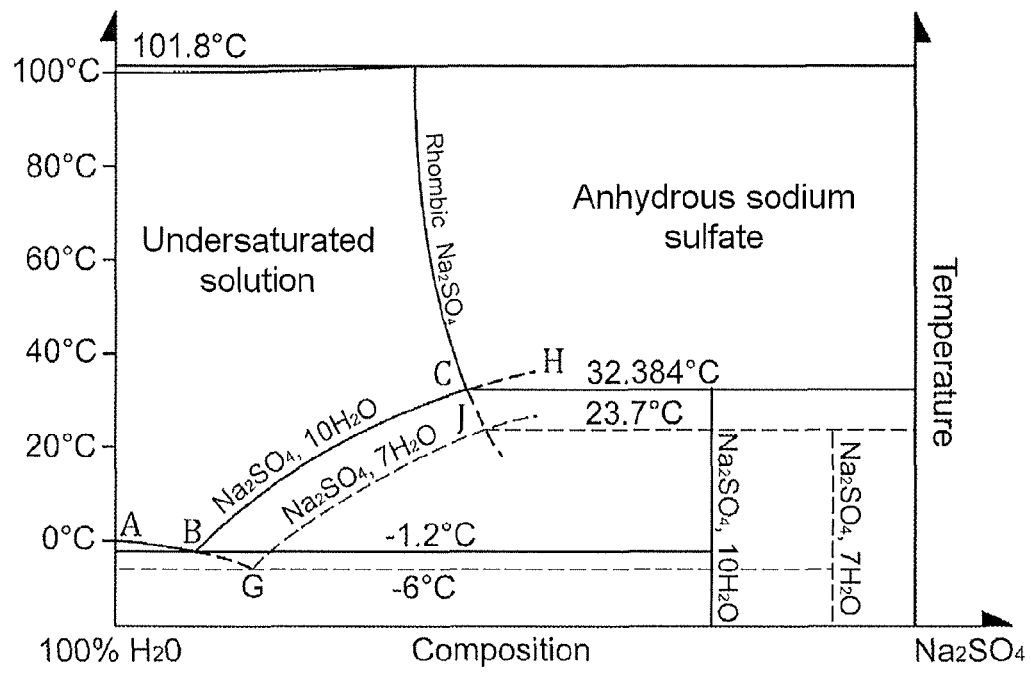
FIG. 6 represents the binary phase diagram of sodium sulfate and of water.

The binary phase diagram of sodium sulfate and of water is represented in FIG. 6. The temperature of the peritectic corresponding to the anhydrous/decahydrate transition is 32.384° C. During the experiment, the maximum temperature measured during this transition is 31.1° C., but by extrapolating the ascending and descending parts of the temperature curve, the curves cross at a temperature of 32.3° C. (FIG. 4). The maximum temperature attained during the transition is therefore very close to that of the stable peritectic invariant.

It is deduced therefrom that device which is the subject of the present patent application makes it possible to obtain valuable information complementary to that obtained by conventional X-ray diffraction analysis. Consequently it is necessary to be able to insert tracking probes into the receptacle.

Figure 7:
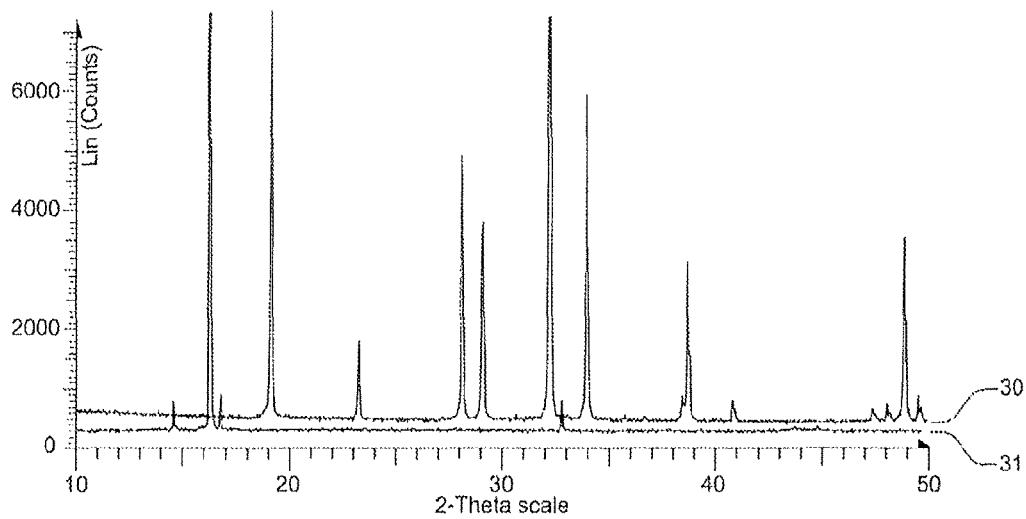
FIG. 7 represents the diffractograms obtained with sodium sulfate decahydrate in aqueous suspension 30 and sodium sulfate decahydrate 31, 20 minutes after filtration.

A sample of the sodium sulfate decahydrate obtained was filtered and left under ambient conditions for 20 minutes and then analyzed by X-ray diffraction on powder. For this analysis the same diffractometer was used. The powder was spread on a frosted glass slide and fixed on the xyz stage. The diffractogram obtained (FIG. 7) shows that the sodium sulfate decahydrate 30 was transformed into anhydrous sodium sulfate 31, thereby showing the efflorescent character of sodium sulfate decahydrate.

It is therefore deduced therefrom that the in situ X-ray diffraction analysis device makes it possible to observe sodium sulfate decahydrate which is efflorescent. Consequently, this device makes it possible to analyze efflorescent phases.

The experimentation carried out shows that the technique of the invention makes it possible to observe efflorescent phases, that is to say phases that are stable when they are in suspension but which become metastable once filtered.

EXAMPLE 2

Tracking of Dehydration with a View to Exploring a Phase Diagram

Figure 8:
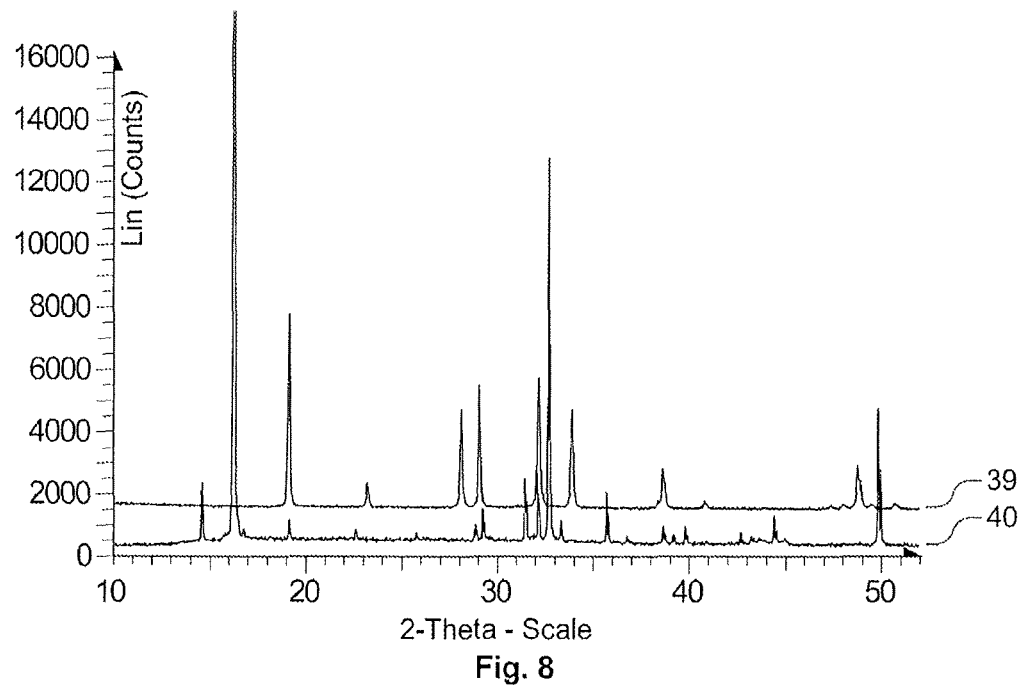
FIG. 8 represents the diffractograms obtained with sodium sulfate decahydrate in aqueous suspension 40 and anhydrous sodium sulfate 39.

The sodium sulfate decahydrate suspension was heated to 33° C. while stirring at 1000 rpm. After stabilization of the temperature, the suspension was analyzed by X-ray diffraction. The diffractogram obtained (FIG. 8) shows that the sodium sulfate decahydrate 40 had evolved into anhydrous sodium sulfate 39. The transformation of anhydrous sodium sulfate into decahydrate is therefore reversible.

The experimentation carried out shows that the technique of the invention makes it possible to observe the dehydration of a hydrate by heating the suspension to a temperature greater than that of the peritectic.

EXAMPLE 3

Tracking of the Evolution of Anhydrous Sodium Sulfate into Sodium Sulfate Heptahydrate with a View to Observing a Metastable Phase In a receptacle of FIG. 2 arranged as shown diagrammatically in FIG. 3, 43.1 g of anhydrous sodium sulfate were added to 70 mL of water heated to 35° C. while stirring at 1000 rpm. The suspension obtained was thereafter cooled from 35° C. to 10° C. in 30 minutes. The temperature and the stirring were performed with the same kit as above.

Figure 9:
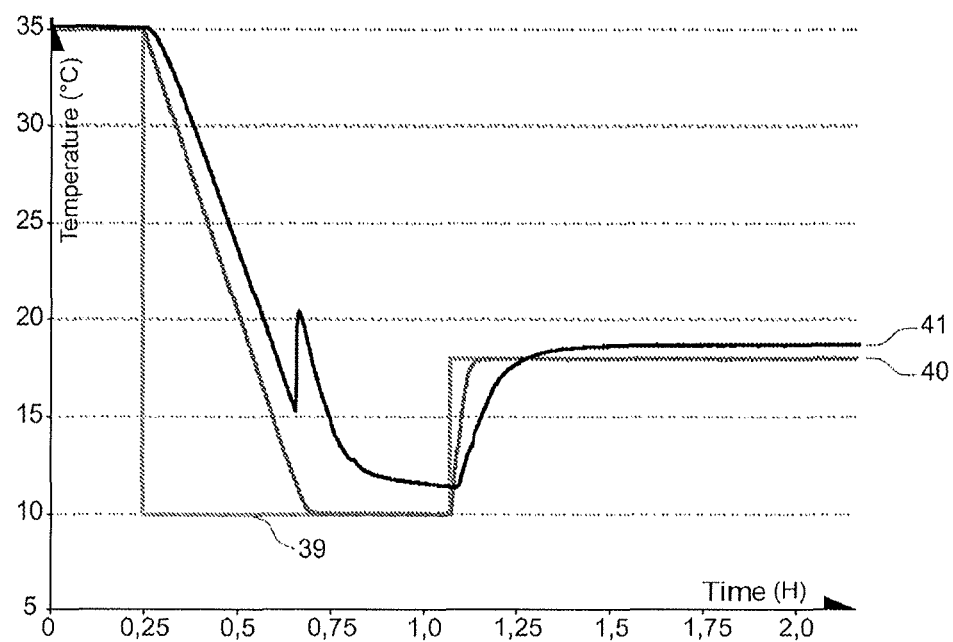
FIG. 9 represents the diffractogram of anhydrous sodium sulfate 39 obtained by heating sodium sulfate decahydrate suspension 40 to 33° C.

The evolution of the temperature was tracked. FIG. 9 represents the temperature programmed in the cryostat 39, the temperature obtained in the bath of the cryostat 40 and the temperature obtained in the receptacle 41 as a function of time. As soon as an exothermic phenomenon was detected (at 11.4° C.), increasing the temperature of the system to 20.5° C., an X-ray diffraction analysis was performed. The analyses are carried out between −10° and −52° in terms of a 2 Theta angular scale, with intervals of 0.038°, the acquisition times being 0.5 s per interval.

The suspension was thereafter stabilized in isotherm at 18° C. while stirring at 900 rpm and X-ray diffraction analyses of the suspension were carried out automatically every hour for 10 hours while continuing to stir the medium at 900 rpm. The analyses are carried out between −10° and −52° in terms of a 2 Theta angular scale, with intervals of 0.038°, the acquisition times being 0.5 s per interval.

FIG. 10, representing the first diffractogram obtained after detection of the exothermic phenomenon, shows that this phenomenon corresponds to the transition of the anhydrous sodium sulfate to sodium sulfate heptahydrate. The peritectic corresponding to the anhydrous/heptahydrate transition is at 23.7° C. (FIG. 6). During the experiment, the maximum temperature attained during this transition is therefore close to the temperature of the metastable peritectic invariant.

FIG. 11 represents the diffractograms recorded during the isotherm at 18° C. as a function of time. The diffractograms obtained show that the sodium sulfate heptahydrate is the only crystalline phase in suspension during the first 4 hours of isotherm 32. After 5 hours at 18° C. while stirring at 900 rpm, the diffractogram obtained corresponds to that of sodium sulfate decahydrate 33. There was therefore a spontaneous transformation of the sodium sulfate heptahydrate into sodium sulfate decahydrate.

It is therefore deduced therefrom that the sodium sulfate heptahydrate is a metastable phase. Consequently, the in situ X-ray diffraction analysis device makes it possible to detect metastable phases and to track their evolutions to more stable phases.

The experimentation carried out shows that the technique of the invention makes it possible to analyze efflorescent phases (stable only when they are in suspension) and metastable phases.

The experimentation carried out also made it possible to track phase transitions: (i). reversible transition from an anhydrous phase to a hydrated phase; (ii). irreversible transition from a metastable phase to a stable phase.

It also shows that the analysis of a suspension while stirring does not alter the quality or the correctness of the results obtained.

It also shows the possibility of coupling the in situ X-ray diffraction analysis with other probes, such as here a temperature probe, to perform specific trackings of the analyzed system (eg: pH probe for tracking acido-basic systems, etc.).

EXAMPLE 4

Tracking of the Crystallization of Pleconaril in Ethanolic Solution with a View to Tracking Polymorphic Transitions In a receptacle of FIG. 2 arranged as shown diagrammatically in FIG. 3 were dissolved 33.73 g of pleconaril in 58.80 g of ethanol at 35° C. The compound was crystallized by cooling from 35° C. to 27.8° C. in 10 minutes while stirring at 900 rpm. The temperature was thereafter maintained at 27.8° C. while stirring at 900 rpm. The temperature and the stirring were performed with the same kit as above.

Once the temperature had stabilized, X-ray diffraction analyses were automatically performed every hour for 20 hours while continuing to stir the medium at 900 rpm. The X-ray source, the sheath, the detector and the control software for the diffractometer as a whole that are used here are those used above. The analyses are carried out between −3° and −30° in terms of a 2 Theta angular scale, with intervals of 0.038°, the acquisition times being 1.0 s per interval.

FIG. 12 presents the diffractograms obtained as a function of time. Initially, the diffractograms show that a mixture of form I and of form III was obtained 34. After 14 hours of isotherm at 27.8° C., form I was totally converted into form III 35. Form I is therefore metastable at this temperature, this being in agreement with the enantiotropic transition from the stable form at low temperature (form III) to the stablest form at high temperature (form I) at 31° C.±2° C. described in the literature (S. Coste, J-M. Schneider, M-N. Petit, G. Coquerel, *Cryst. Growth Des.*, 2004, 4(6), 237-244).

This example shows that the analysis technique of the invention makes it possible to observe and to carry out kinetic tracking of polymorphic transitions.

EXAMPLE 5

Tracking of the Monotropic Transition of D-Mannitol

In a receptacle of FIG. 2 arranged as shown diagrammatically in FIG. 3 were dissolved 4.5 g of beta form of D-mannitol in a water/methanol mixture, containing 48.1 mL of ethanol and 39.5 mL of water, at 40° C. while stirring at 1200 rpm. The solution obtained was cooled from 40° C. to 15° C. in 30 minutes without there being any spontaneous nucleation. 30 mL of methanol were thereafter added rapidly to this solution. The temperature of the system was thereafter adjusted to 20° C. while continuing to stir at 1200 rpm. The temperature and the stirring were performed with the same kit as above.

Once the temperature had stabilized, X-ray diffraction analyses were performed every hour for 16 hours while continuing to stir the medium at 1200 rpm. The X-ray source, the sheath, the detector and the control software for the diffractometer as a whole that are used here are those used above. The analyses are carried out between −3° and −30° in terms of 2Theta, with intervals of 0.038°, the acquisition times being 1.0 s per interval.

The diffractograms obtained are presented as a function of time in FIG. 13. The first diffractogram obtained on the suspension at 20° C. shows that the addition of the antisolvent (methanol) to the supersaturated solution at 15° C. brought about the crystallization of the delta form of D-mannitol 36. After 4 hours of isotherm at 20° C., the first peaks of the beta form were observed on the diffractogram 37. Complete transition was observed after 13 hours of isotherm 38.

The delta form of D-mannitol is therefore the metastable form at 20° C. Indeed, D-mannitol exhibits a system having monotropic character, that is to say that a polymorphic form is metastable whatever the temperature and pressure conditions. The beta form is the stablest form of D-mannitol in the temperature and pressure domain studied.

The technique of the invention implemented on suspensions in equilibrium with their mother liquors therefore makes it possible to study the relative stabilities of the polymorphs when they are in suspension.

EXAMPLE 6

Tracking of the Hydration of BrHPP Benz at 5 and 25° C.

A preliminary study of the behavior of the benzathine salt of a bromohydrin pyrophosphate (BrHPP Benz hereinafter, Coquerel, G.; Aubin, E. Phosphoantigen Salts of Organic Bases and Methods for their Crystallization. Purification by means of crystallization of some Pyrophosphate analogous antigen. U.S. patent No. 60/724,308, Jun. 10, 2005, 2005) as a function of relative humidity was carried out by DVS (Dynamic Vapor Sorption). This study has shown that BrHPP Benz hydrates into BrHPP Benz, $2H_2O$ onward of 62% Relative Humidity (RH) at 25° C. and onward of 58% RH at 5° C.

Similar analyses were carried out by virtue of the arrangement represented in FIG. 3. Hydration is detected by tracking carried out by X-ray diffraction at variable humidity for two different temperatures.

Humid gas:

In a receptacle as presented in FIG. 14, a few milligrams of anhydrous BrHPP Benz powder were deposited at the center of the X-ray-transparent window, so as not to be in contact with the walls of the receptacle. The internal temperature of the receptacle was regulated by a first thermostat (F32-HE®) marketed by Julabo) via the double jacket of the receptacle.

Air controlled in terms of humidity and temperature sweeps the powder.

Regulation in terms of humidity was carried out by virtue of a humidity generator (Wetsys® marketed by Setaram). The thermo-regulation of the humid gas was carried out by circulating in a pipe (teflon, length: 2 meters, internal diameter 3 mm) placed in the enclosure of the receptacle. The temperature of the enclosure was adjusted so that the temperature of the humid air above the powder is at the desired temperature.

External gas:

Dry air is pumped and sent onto the exterior face of the X-ray-transparent window. This dry air is thermo-regulated by a counter-current heat exchanger connected up to a second thermostat (polystat cc2®, marketed by Huber). The temperature of this second thermostat is parameterized so that the dry gas at the level of the exterior of the membrane transparent to XR is at the same temperature as that of the upper face in the chamber wherein lie the crystals of BrHPP Benz to be analyzed.

a) Study of the hydration of BrHPP Benz at 25° C.:

The temperatures of the internal humid gas and of the external dry gas are regulated to 25° C. A diffraction diagram is recorded every hour.

Parameters:

internal gas: —Temperature $T_{humid\ air\ in\ contact\ with\ the\ powder}=25°\ C.$ Flow rate $Q_{humid\ air}=50$ mL/min external gas: —Temperature $T_{external\ air}=25°\ C.$ Flow rate $Q_{dry\ air}=70$ L/h.

The diffractograms obtained during tracking (FIG. 15) show that the transition from anhydrous to dihydrate begins between a relative humidity (RH) of 62 and 63% at 25° C.

This result is in agreement with the DVS analysis carried out at 25° C.

b) Study of the hydration of BrHPP Benz at 5° C.:

Three trials are carried out to show the importance of the thermo-regulated external dry gas:

without external dry gas, with the external dry gas but not thermo-regulated, with the external dry gas thermo-regulated.

Inside the receptacle, the humid gas is regulated to 5° C.

Without external dry gas:

Parameters:

Internal gas: —$T_{humid\ air\ in\ contact\ with\ the\ powder}=5°\ C.$ $Q_{humid\ air}=50$ mL/min

| % RH at 5° C. | 0 | 47.7 | 51.2 | 55.1 | 59 | 63.3 | 67.6 | 72.4 | 77.6 | 83.2 | 88.9 | 95 |
|---|---|---|---|---|---|---|---|---|---|---|---|---|
| Duration (H.) | 1 | 1 | 1 | 1 | 1 | 1 | 1 | 1 | 1 | 1 | 1 | 4 |

The diffractograms obtained show that the intensity of the signal is decreasing, without the evolution to the dihydrated phase occurring.

With external dry gas not thermo-regulated
Parameters:
  Internal gas: —$T_{humid\ air\ in\ contact\ with\ the\ powder}$=5° C.
    $Q_{humid\ air}$=50 mL/min

| % RH at 5° C. | 0 | 47.7 | 51.2 | 55.1 | 59 | 63.3 | 67.6 | 72.4 | 77.6 | 83.2 | 88.9 | 95 |
|---|---|---|---|---|---|---|---|---|---|---|---|---|
| Duration (H.) | 1 | 1 | 1 | 1 | 1 | 1 | 1 | 1 | 1 | 1 | 1 | 4 |

External gas: —$T_{external\ air}$=28° C.
  $Q_{dry\ air}$=70 L/h.

According to the diffractograms recorded every hour (FIG. 16), at 5° C., the humidity threshold for observing the anhydrous→dihydrate transition is situated near 95% by X-ray diffraction tracking with the exterior gas stream not thermo-regulated. This result is in profound disagreement with the DVS study (58% RH at 5° C.).

With thermo-regulated external dry gas
Parameters:
  Internal gas: —$T_{humid\ air\ in\ contact\ with\ the\ powder}$=5° C.
    $Q_{humid\ air}$=50 mL/min

| % RH at 5° C. | 0 | 47.7 | 49.4 | 51.2 | 53.3 | 55.2 | 56.8 | 59 | 61.1 | 63.3 | 65.5 | 67.6 |
|---|---|---|---|---|---|---|---|---|---|---|---|---|
| Duration (H.) | 1 | 1 | 1 | 1 | 1 | 1 | 1 | 5 | 1 | 1 | 1 | 1 |

External gas: —$T_{external\ air\ on\ the\ window}$=5° C.
  $Q_{dry\ air}$=70 L/h.

According to the diffractograms recorded every hour (FIG. 17), at 5° C., the humidity threshold for observing the anhydrous→dihydrate transition is situated near 59% by X-ray diffraction tracking with a thermo-regulated exterior gas stream.

This result is indeed in agreement with the DVS study (RH 58% for 5° C.).

In the absence of external gas, or when the latter is not thermostatically controlled to the temperature of the analysis, the results are erroneous. It is therefore important to send a thermo-regulated gaseous stream onto the exterior part of the receptacle carrying the sample so as to ensure temperature homogeneity at the level of the analyzed powder.

The invention claimed is:

1. A method of measuring scattering of X-rays, characterized in that a compound to be analyzed is installed in a receptacle comprising an X-ray-permeable flat bottom, in that an X-ray diffraction analysis is undertaken by sending an X-ray stream upwards toward said X-ray-permeable bottom and by measuring a stream of scattered X-rays reflected downwards, and in that a fluid thermostatically controlled to the same temperature as that of the compound to be analyzed in the receptacle is projected toward the X-ray-permeable flat bottom, from outside the receptacle.

2. The method as claimed in claim 1, characterized in that the X-ray-permeable flat bottom is installed horizontally.

3. The method as claimed in claim 1, characterized in that an angle of incidence of the X-ray stream is made to vary from -0.5 degrees to -70 degrees in terms of a 2 Theta angular scale.

4. The method as claimed in claim 1, characterized in that the receptacle is provided with a thermoregulating device.

5. A method for the tracking of a crystallization process which utilizes the method of claim 1.

6. A method for the tracking of a polymorphic or solvation evolution which utilizes the method of claim 1.

7. A method for the study of the stability of a solid phase in a liquid, gas, gel, emulsion or amorphous solid matrix which utilizes the method of claim 1.

8. A method for the search for metastable phases or reaction intermediaries which utilizes the method of claim 1.

9. A method for the study of the evolution of a salt as a function of pH which utilizes the method of claim 1.

10. A method for the study of the evolution of a salt in a solvent as a function of the composition in solvent and/or in constituents of all sorts liable to give rise to the formation of a solid which utilizes the method of claim 1.

11. A device for measuring scattering of X-rays, characterized in that it comprises a receptacle comprising a bottom plugged by an X-ray-transparent membrane, as well as a diffractometer provided with a goniometer installed so as to direct a beam of X-rays from underneath toward the X-ray-transparent membrane and a detector being installed for the measurement of the X-rays scattered from underneath, and in that the receptacle comprises means for heating or cooling a compound to be analyzed;
  wherein the receptacle comprises outside the receptacle one or more nozzles for projecting a fluid thermostatically controlled to the same temperature as that of a compound to be analyzed in the receptacle, toward the x-ray-transparent membrane, from outside the receptacle, the receptacle comprising an internal temperature probe serving to match the temperature of the compound to be analyzed and that of the fluid.

12. The device as claimed in claim 11, characterized in that the bottom of the receptacle comprises a circular opening plugged by the X-ray-transparent membrane.

13. The device as claimed in claim 11, characterized in that the X-ray-transparent membrane is flat.

14. The device as claimed in claim 11, characterized in that the X-ray-transparent membrane is made of polyimide or of polyethylene terephthalate.

15. The device as claimed in claim 11, characterized in that it comprises one or more probes.

16. The device as claimed in claim 11, characterized in that it comprises a platform mobile in the three directions x, y and z in space as a consequence of which it is possible to adjust the location of the X-ray-transparent membrane.

* * * * *